United States Patent [19]
Reed et al.

[11] Patent Number: 5,985,273
[45] Date of Patent: Nov. 16, 1999

[54] BIOLOGICAL CONTROL OF INSECTS

[76] Inventors: Benjamin J. Reed, 19 Frederick Street, Ferntree Gully, Victoria; Richard M. Sandeman, Plenty Road, Bundoora, Victoria; David S. Chandler, Brassey Court, Mickleham, Vicotria, all of Australia

[21] Appl. No.: 08/765,165

[22] PCT Filed: Jun. 15, 1995

[86] PCT No.: PCT/AU95/00347

§ 371 Date: Jun. 27, 1997

§ 102(e) Date: Jun. 27, 1997

[87] PCT Pub. No.: WO95/35031

PCT Pub. Date: Dec. 28, 1995

[30] Foreign Application Priority Data

Jun. 17, 1994 [AU] Australia ................. PM 6313
Jul. 15, 1994 [AU] Australia ................. PM 6876

[51] Int. Cl.⁶ .................... A61K 38/48; A61K 38/00; C12N 9/48
[52] U.S. Cl. .................... 424/94.63; 435/212; 514/12
[58] Field of Search .......... 424/94.63; 435/212; 514/12

[56] References Cited

U.S. PATENT DOCUMENTS

| | | | |
|---|---|---|---|
| 5,045,460 | 9/1991 | Martineau et al. | 435/172.3 |
| 5,262,178 | 11/1993 | Camine et al. | 424/94.67 |
| 5,356,622 | 10/1994 | Heath et al. | 424/265.1 |
| 5,449,662 | 9/1995 | Scarborough | 514/117 |
| 5,560,937 | 10/1996 | Lee et al. | 424/569 |
| 5,712,143 | 1/1998 | Grieve et al. | 435/212 |

FOREIGN PATENT DOCUMENTS

| | | |
|---|---|---|
| 3656889 | 12/1989 | Australia . |
| 631551 | 12/1992 | Australia . |
| WO 92/21753 | 12/1992 | WIPO . |
| WO 94/16565 | 8/1994 | WIPO . |

OTHER PUBLICATIONS

Baker, Digestive Proteinases of Sitophilus weevils (Coleoptera: Curculionidae) and Their Response to Inhibitors from Wheat and Corn Flour, Can. J. Zool. 60:3206–3214, 1982.

Ferreira and Terra, Substrate Specificity and Binding Loci for Inhibitors in an Aminopeptidas Purified from the Plasma . . . Cells of an Insect Larva, Archives of Biochemistry and Biophysics 244:478–485, 1986.

Ryan, Protease Inhibitors in Plants: Genes for Improving Defenses Against Insects and Pathogens, Ann. Rev. Phytopathol. 28:425–49, 1990.

Burgees, E. P. J., et al., "Effects of Protease Inhibitor Concentration and Combinations on the Survival, Growth and Gut Enzyme Activities . . . ," J. Insect Physiol., vol. 40, No. 9, pp. 803–811 (1994).

Christeller, J. T., et al., "Midgut Proteast Activities in 12 Phytophagous Lepidopteran Larvae: Dietary and Protease Inhibitor Interactions," Insect Biochem. Molec. Biol., vol. 22, No. 7, pp. 735–746 (1992).

Christeller, John T., "The Interaction of the Elastase Inhibitor, Eglin c, with Insect Digestive Endopeptidases: Effect of pH . . . ," Insect Biochem. Molec. Biol, vol. 24, No. 1, pp. 103–109 (1994).

Dymock, J. J., "Behavioural and physiological responses of grass grub larvae (*Costelytra zealandica*) feeding on protease inhibitors," New Zealand Journal of Zoology, vol. 19, pp. 123–131 (1992).

Wolfson, J. L., "Suppression of larval Colorado potato beetle growth and development by digestive proteinase inhibitors," Entomol. exp. appl., vol. 44, pp. 235–240 (1987).

*Primary Examiner*—Jon P. Weber
*Attorney, Agent, or Firm*—Fish & Richardson P.C.

[57] ABSTRACT

The invention relates to composition and methods of use thereof for controlling insects. The compositions comprise aminopeptidase inhibitors or metallopeptidase inhibitors and further comprise a non-strongly-chelating peptidase inhibitor. The compositions are preferably applied topically, and preferably cause inhibition of hatching of insect eggs and/or inhibition of the development and/or mortality of insect larvae.

40 Claims, No Drawings

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: synthetic substrates

<400> SEQUENCE: 1

Ala Ala Pro Leu

BIOLOGICAL CONTROL OF INSECTS

This invention relates to a method of controlling insects and to compositions therefor.

In particular the invention relates to the control of infestations by insects of animals or plants, and to the prophylaxis of infections of animals or plants which are transmitted by insects. The invention is also applicable to the amelioration of infections which are consequential upon infestation by insects.

More particularly the invention relates to the use of compositions comprising peptidase inhibitors for the control of insects, and to the use of insect-resistant transgenic organisms which express peptidase inhibitors.

BACKGROUND OF THE INVENTION

Insects cause significant pest problems in a wide variety of animals and plants worldwide, with estimates of 13% of crop production lost each year despite current control measures. Insect species of the orders Lepidoptera, Hemiptera, Orthoptera, Coleoptera, Psocoptera, Isoptera, Thysanoptera and Homoptera cause massive losses to many horticultural and broadacre crops and stored and manufactured grain products. Diptera, Anaplura, Malophaga and Siphonaptera cause parasitic infections in animals and man. Other orders (Hymenoptera, Dictyoptera, Isoptera) include important domestic and industrial pests.

Many of the known control measures for insects depend on the use of chemical insecticides, for example chlorinated hydrocarbons (DDT, endosulfan etc), organophosphates (chlorpyrifos, diazinon, malathion, parathion), organocarbamates (carbaryl, methomyl, proxypur) and synthetic pyrethroids (cypermethrin, deltamethrin).

Problems associated with the use of chemical insecticides include the development of resistance by target insects (organophosphates, synthetic pyrethroids), the persistence of the chemicals in the environment and in plant and animal tissues, and the harmful effects on non-target organisms (organochlorines, insect growth regulators).

Boron compounds (borax, polybor) have also been used for insecticidal purposes. Boron compounds are stable, kill insects relatively slowly at practical doses (Mullens and Rodriguez, 1992), and ingestion of large doses by humans can be lethal (Anon, 1991)

Other categories of insecticide include insect growth regulators (IGRs) and insecticidal bacterial toxins (eg. *Bacillus thuringiensis* (Bt) toxins). IGRs are compounds that interfere in some way with chitin synthesis. They include juvenile hormone analogues (methoprene), chitin synthesis inhibitors (fenoxycarb, diflubenzuron, flurazuron) and triazine derivatives (cyromazine). Resistance has been noted to many classes of IGR. Resistance is also developing in certain lepidoterans to Bt toxins. It is technically difficult with both IGRs and Bt toxins to ensure adequate insect kill at an appropriate stage in its life cycle. Some IGRs are stable and may pose environmental hazards.

The most useful groups of insecticides are those having high insecticidal activity and low environmental persistance (organophosphates, synthetic pyrethroids). The greatest problem associated with these, however, is the development of resistance by target insects. It is believed that 90% of insecticide use is still based on classical neurotoxic insecticides. The search for alternative low-residual insecticides which are effective on insects resistant to existing insecticides is thus particularly urgent.

Agents referred to as synergists may be used to maximise effectiveness of particular insecticides. Synergists may or may not be insecticidal in their own right. Blood and Studdert (1988) define a synergist as an agent that acts with or enhances the action of another. As an example, it may be noted that piperonyl butoxide is a synergist for synthetic pyrethroids. Synergists which are effective in combination with a particular insecticide may not be effective in combination with other insecticides. Synergists can be used to overcome problems of insect resistance, although insect resistance to synergists can also occur. The role of synergists in insecticidal formulations can be vital for achieving a commercially viable result, and for insecticide resistance management. The search for effective synergising combinations is as urgent as the search for effective insecticides per se (Forrester et al, 1993).

Recently attention has focused on insect peptidases, inhibition of which may provide a possible means of insect control. Peptidases are ubiquitous enzymes which break down proteins and peptides, and thus assist with digestion both in the gut and in cells. They are involved in tissue reorganisation during embryo development, moulting and pupation in insects. They are also involved with defence against invading organisms and with protein regulation.

Peptidases are a widely variable group of enzymes. Currently they are classified according to:

(1) the reaction catalysed (2) the chemical nature of the catalytic site, and (3) the evolutionary relationship as revealed by structure (Barrett, 1994)

The International Union of Biochemistry and Molecular Biology (IUBMC), In:Enzyme Nomenclature (1992), classifies peptidases by enzyme class (EC) categories. These categories are EC 3.4.11 to 3.4.19 for exopeptidases (those enzymes that only act near the ends of peptide chains) and EC 3.4.21 to 3.4.99 for enzymes that preferentially act on the inner regions of peptides. Group EC 3.4.99 is a group of peptidases for which the catalytic mechanism is unrecognised or uncharacterised.

An overview of the peptidase classes and their relationship to insect biochemistry is outlined below.

1. Serine Peptidases

This group includes serine-type carboxypeptidases EC 3.4.16, and serine endopeptidases EC 3.4.21.

Serine peptidases are typically recognised by a catalytically active serine amino acid at their active site, and by their sensitivity to an enzyme inhibitor, 3,4-dichloroisocoumarin (3,4-DCI). The preferred pH range for activity of mammalian serine peptidases is 2–8; however insect serine peptidases are commonly adapted to alkaline conditions (pH 9 to over 11 in some lepidopteran larvae).

The activity of serine peptidases in insects is also commonly defined by reaction of the enzymes with synthetic substrates. The three common categories of insect serine peptidases (trypsin-like, chymotrypsin-like and elastin-like) can be identified in this way. Trypsin-like serine peptidases react with synthetic substrates P-tosyl-L-arginine methyl ester (TAME), α-N-benzoyl-L-arginine ethyl ester (BAEE), α-N-benzoyl-DL-arginine-p-nitroanilide (BAPNA) and benzoyl-DL-arginine naphthylamine (BANA).

Chymotrypsin-like peptidases may be identified by their reaction with:

N-acetyl-L-phenylalanine ester (APNE)

N-acetyl-L-tyrosine ethyl ester (ATEE)

N-benzoyl-L-tyrosine ethyl ester (BTEE)

N-benzoyl-L-tyrosine-p-nitroanilide (BTPNA)

L-glytaryl-L-phenylalanine-p-nitroanilide (GPPNA)

N-succinyl-L-phenylalanine-p-nitroanilide (SPAPNA)
L-glutaryl-L-phenylalanine naphthylanide (GPNA).

Elastase-like serine peptidase inhibitors may be identified by their reaction with synthetic substrates such as N-succinyl-ala-ala-pro-leu p-nitroanilide (SAAPLpNA) (SEQ ID NO:1)

The activity of serine peptidases may also be described in terms of their reaction with enzyme inhibitors. Serine-group peptidases are generally inhibited by Di-isopropyl-flurophosphate (DipF/DFP), and paraphenyl methyl sulphonyl fluoride (PMSF). Trypsin-like peptidases are inhibited by tosyl-L-lysine chloromethyl ketone (TLCK). Chymotrypsin-like peptidases are inhibited by tosyl-L-phenylalanine chloromethyl ketone (TPCK). Elastase-like peptidases are inhibited by Eglin-C.

A number of naturally occurring proteins have been found to be able to inhibit serine peptidases. These include the crystalline soybean trypsin inhibitor of Kunitz (SBTI) and the soybean trypsin inhibitor of Bowman-Birk (BBTI). Various other legume seeds contain peptidase inhibitor at 1–4% of total protein, for example chickpea trypsin/chymotrypsin inhibitor (CI), Lima Bean trypsin inhibitor (LBTI) and cowpea trypsin inhibitor (CPTI) (MacIntosh et al, 1990). Animal-derived serine peptidase inhibitors include bovine pancreatic trypsin inhibitor (BPTI, Aprotinin), egg-derived ovomucoid and alpha-1-antitrypsin from blood.

Serine peptidases having alkaline pH optima are recognised to be of primary importance as soluble enzymes in the digestive fluids of insects. Examples include sphingidae (Miller et al, 1974), noctuidae (Ahmed et al. 1976, 1980; Ishaaya et al, 1971; Prichet et al, 1981; Teo et al, 1990; Broadway and Duffy, 1986), bombycidae (Sasaki and Suzuki, 1982; Euguchi and Iwanito, 1976; Euguchi and Kuriyama, 1985), pieridae (Lecadet and Dedonder, 1966; Broadway et al, 1989) pyralidae (Larocque and Houseman, 1990; Houseman et al, 1989; Mohammed and Altias, 1987) and diptera (Bowles et al, 1990). Cristeller et al (1992) showed that serine peptidases were implicated in the (casein) digestive activity of twelve phytophagous lepidopterans. In this article Christeller found that no other type of peptidase showed significant evidence of digestive activity. Serine peptidases have also been found to exhibit a dominant role in keratin-digesting lepidopterans (Christeller et al, 1994; Prowning and Irzykiewicz 1962; Ward, 1975 a, b). Furthermore, they have an important role in the digestive activity of some coleopterans (McGhie et al, 1995, Dymock et al, 1992), some orthopterans (Sakal et al, 1989; Christeller et al, 1990), some heteropterans (Cohen 1993) and in some dipterans (Bowles et al, 1990).

The digestive serine peptidases vary considerably both in number and in catalytic properties within and between species (Applebaum, 1985). In some instances inhibitors of serine peptidases in insect diets have been recognised to cause feeding deterrence as well as digestive inhibition (Dymock et al, 1992).

Trypsin-like serine peptidases have been recognised to be involved in the key growth regulatory area of molting. They exhibit several roles including process control, exposure of chitin fibrils to chitinase enzymes and in recycling of cuticular material (Samuels and Paterson, 1991).

Because of their dominant metabolic roles, their common natural occurrence, and the occurrence of many natural inhibitors in plants and animals, serine peptidases have received the most attention as agents for insect control. It is important to note that the context for use of serine peptidases in insect control has almost entirely been in the area of transgenic plants.

2. Cysteine (Thiol) Peptidases

This group includes cysteine-type carboxypeptidases (EC 3.4.18) and cysteine endopeptidases (EC 3.4.22).

These enzymes are characterised by possession of a catalytically active cysteine residue at their active site and by their sensitivity to certain inhibitors. Cysteine peptidases are characteristically activated under reducing conditions (added cysteine, dithiothreitol or other reducing agents). Cysteine peptidases are soluble enzymes generally found in midgut contents of insects. Mammalian cysteine peptidases commonly function in low pH conditions, although in insects, near neutral or mildly acidic pH values are favoured (Wolfson and Murdock, 1987).

The activity of cysteine peptidases is exemplified by their reaction with synthetic substrates n-α-benzoyl-L-arginine-p-nitroanilide (BAPNA) or benzoyloxy carbonyl-phe-arg-7-(4 methyl) coumaryl amide (Z-Phe-Arg-MCA). The activity of cysteine peptidases may also be described in terms of their reaction with enzyme inhibitors such as iodoacetamide, iodoacetate, heavy metals, p-chloromercuribenzoate, cystine cyanide, N-ethyl maleimide and characteristically, E-64. E-64 is a small peptide (L-trans-epoxy-succinyl-leucylamido-(4-guanidino-butane) obtained from a strain of *Aspergillus japonicus*. Naturally occurring cysteine peptidase inhibitors have been identified in microbes (E-64), plants (oryzacystatins I and II from rice grains and potato multicystatin (PMC) from potato tubers), and animals (hen-egg cystatin, HEC). Antipain is another well-known cysteine peptidase inhibitor.

Cysteine peptidases play a major role as soluble digestive enzymes of the gut of some insects, notably coleopterans (Orr et al, 1994; Thie and Houseman, 1990; Liang et al, 1991). The use of cysteine peptidase inhibitors for the control of insects has been largely explored in the context of transgenic plants (Orr et al, 1994; Wolfson and Murdock, 1987).

3. Aspartic Peptidases (EC 3.4.23)

These enzymes are typically recognized as possessing two aspartyl residues at the active site. Many aspartic peptidases are most active at low-pH values. Synthetic substrates for these enzymes include N-carbobenzoxy glutamyl-L-tyrosine and N-acetyl-L-phenanyl diiodotyrosin. Characteristic inhibitors for aspartic peptidases include pepstatin and diphenyl diazomethane (McDonald, 1985). Pepstatin is a naturally occurring inhibitor from a microbial source.

Applebaum (1985) has suggested some significance of aspartic peptidases to dipterans. Wolfson and Murdock (1987) have demonstrated some growth inhibition of a coleopteran (Colorado potato beetle larvae) by pepstatin; however, greater inhibition of growth was obtained by targeting cysteine peptidases.

An extensive search of the literature on peptidases has shown that only a limited amount of research has been conducted on insect aspartyl peptidases for insect control, either by transgenic modification of plants or by topical application. Christeller et al (1992) found that aspartic peptidase activity is apparently not evident in phytophagous lepidopteran gut material.

4. Metallopeptidases

These enzymes are typically recognised as possessing a catalytically active metal ion (commonly zinc) at the active site, and by their sensitivity to chelating agents. The metallopeptidase category includes some endopeptidases (enzymes that cleave within the peptide chain) and exopeptidases (enzymes that cleave amino acid(s) from the termini of peptides). Exopeptidases can further be categorised as carboxypeptidases (which cleave amino acid(s) from the C terminus) or aminopeptidases (which cleave amino acids from the N terminus).

Metallo endopeptidases (EC 3.4.22)

These enzymes have not been implicated in insect biochemistry, except for a possible role in wool digestion by keratinophagous lepidopterans (Prowning and Irykiewicz, 1962; Ward, 1975 a and b; Christeller et al, 1990, 1994).

Metallo carboxypeptidases (EC 3.4.17)

Metallo carboxypeptidases require a bivalent cation (usually $Zn^{2+}$) for activity. They exist in both free and membrane-bound forms and favour activity at high (8–10) pH. Synthetic substrates for carboxypeptidases include hippuryl-DL-phenyl-lactic acid and hippuryl-L-arginine, for carboxypeptidase type A and B, respectively. Carboxypeptidase A-like enzymes appear to be more common in insects, and have been found in orthopterans, coleopterans, dipterans and lepidopterans.

Synthetic inhibitors for metallo carboxypeptidases include 1,10-phenanthroline, ethylene diamine tetraacetic acid (EDTA), β-hydroxyquinoline and phosphoramidon. A naturally occurring inhibitor for metallo carboxypeptidase is potato-derived carboxypeptidase inhibitor (PCPI).

Carboxypeptidase enzymes in both free and membrane-bound forms have been recognised in mid-gut material from lepidopteran larvae (Ferreira et al, 1994; Christeller, 1990). Christeller et al (1992) described these enzymes as expected components of the protein digestion system. Prior to the priority date of this application these enzymes were not apparently recognised as targets for transgenic modification of plants, let alone as components of topical control agents.

Aminopeptidases (EC 3.4.11–3.4.13)

Aminopeptidases hydrolyse amino acids from the N-terminus of peptide chains, and are generally classified according to their dependence on metal ions ($Zn^{2+}$ or $Mg^{2+}$). The best studied aminopeptidases are found in the digestive tracts of mammals in both membrane bound and soluble forms. Aminopeptidases are commonly named with a suffix letter designating their pH optima, acidic (A) basic (B) or neutral (N), or by their membrane bound (M) state or by the number and type of amino acids cleaved from peptide substrates. These names are not exclusive; thus a leucine aminopeptidase M or N is an enzyme that preferentially but not exclusively removes leucine from a peptide, is membrane bound and whose activity is optimal at neutral pH. Aminopeptidases show preferential hydrolysis of leucyl, arginyl, methionyl, aspartyl, alanyl, glutamyl, prolyl, valyl and cysteinyl residues; however, substrate specificity is usually broad, and also depends on the other residues in the peptide chain (Taylor, 1993 a and b). Most aminopeptidases are metallopeptidases, although a few bacterial enzymes are known not to require metal ions for activity (Taylor, 1993 a and b). There are apparently few natural inhibitors of aminopeptidase.

Insect aminopeptidases usually have alkaline pH optima and are generally inhibited by bestatin (Taylor, 1993) and phenanthroline (Barrett, 1994).

Substrate specificities are broad, as stated above, but typical substrates include leu-pNA, arg-pNA, met-pNA and pro-pNA.

Metallo aminopeptidases are inhibited by chelating agents (such as EDTA), which can either remove the metal ion from the peptidase or form an inactive complex with the enzyme (Terra & Ferriera, 1994). The action of a particular chelator will vary with the type of aminopeptidase as well as with the chelator's own structure.

Aminopeptidases have been also recognised as part of the insect complement of digestive peptides, and are thought to be involved in the terminal stages of protein digestion (Terra & Ferriera, 1994). Christeller et al (1990, 1992) has asserted that exopeptidases (including aminopeptidases) will be of little use for insect control because of the minor role of these enzymes in the digestion of dietary protein relative to serine and cysteine peptidases.

Insect larval growth retardation following exposure to specific leucine aminopeptidase (LAP) inhibitors has not been reported. Christeller et al (1990) have shown with crude field cricket gut extracts that although exopeptidase levels, particularly LAP, are significant in this insect, exopeptidases contributed only 16–20% of protein digestion. In Christeller's study, it was further found that in the presence of two effective serine peptidase inhibitors, the contribution of exopeptidases to protein digestion was greatly reduced. This was attributed to lack of oligopeptide chain ends to act as substrates for exopeptidases. This further indicated a minor role for aminopeptidases in insect control.

The above findings teach strongly away from the use of exopeptidase inhibitors (principally aminopeptidase inhibitors) as insect control agents, and teach particularly strongly away from the combined use of serine peptidase inhibitors and aminopeptidase inhibitors as insect control agents.

Apart from a digestive role, aminopeptidase activity has been demonstrated in the moulting fluid of the lepidopteran *Manduca sexta* (Jungries, 1979). However, again the role of aminopeptidases appears to be secondary to the role of serine (trypsin-like) peptidases. No naturally occurring inhibitors of aminopeptidases or metallopeptidases important in insect development have been reported as effective in retardation of moulting. None have been used to provide insect-resistant transgenic plants.

Theoretically there appears to be a high potential for using peptidase inhibitors to control insects which are resistant to chemical insecticides. Firstly, the mechanism of action of peptidase inhibition is different from the mechanism of action of organophosphates and synthetic pyrethroids. Secondly, the amino acid sequence of the active sites of peptidase enzymes appears to be highly conserved (Taylor, 1993), thus indicating a low potential for mutation without consequent loss of activity. Finally, in the event that insect resistance to a particular peptidase inhibitor occurs, this resistance should not carry over to other peptidase mediated metabolic events.

However, there are significant problems associated with the use of peptidase inhibitors for the control of insects. High use rates may be required, leading to a product which is not cost-effective. Furthermore, whilst the peptidase inhibitor may limit larval growth, it is possible that a plateau is reached in the dose-response curve, even at elevated use rates. Peptide-based or protein-based peptidase inhibitors, while presumably non-residual in the environment, may be difficult to store over extended periods, and may lose efficacy when delivered in hard water. Subtle issues involving the source of a particular enzyme inhibitor may need to be addressed. For example, anomalous responses involving growth inhibition of *Costelytra zealandica* by soybean, potato and cowpea trypsin inhibitor and growth stimulation by lima bean trypsin inhibitor have been noted (Dymock et al, 1992).

Considerable research has centred on biochemical investigations of insect protein metabolism, principally digestive metabolism, using insect tissues, gut extracts, semi-purified or purified enzymes in vitro.

Much of this work has been directed toward the selection of enzyme inhibitors for the transgenic modification of plants by investigating the relationship of digestive enzymes with protein or peptide based inhibitors (Applebaum, 1985; Christeller et al, 1989, 1990, 1992; Lenz et al, 1991; Teo et al, 1990; Pritchett et al, 1981, Santos and Terra, 1984; Dow, 1986; Sakal et al, 1984, 1989).

Relatively fewer studies demonstrate a direct adverse influence of peptidase inhibitors on insect growth and/or reproduction. Serine and cysteine peptidase inhibitors have been shown to reduce the larval growth and/or survival of various insects, including *Callosobruchus macalatus, Leptinotarsa decemlineata, Heliothis spp, Spodoptera exiqua, Costelytra zealandica, Teleogryllus commodus, Diabrotica sp, Manduca sexta,* red four beetle and bean weevil (Gatehouse and Boulter, 1983; Shuckle and Murdock, 1983; Shade et al, 1986; Wolfson and Murdock, 1987; Broadway and Duffey, 1986; Hilder et al, 1987; Dymock et al, 1992; Orr et al, 1994; Burgess et al, 1994; Hines et al, 1990).

Generally insect growth inhibition has been achieved with inhibitors of principal digestive enzymes of the gut, and a method for selection of appropriate insecticidal inhibitors based on these enzymes has been described by Christeller et al (1992).

None of the above studies appears to be directly aimed at the production of topical insect control agents through interference with protein metabolism. In International Patent Application No. W094/16565 by Czapla, however, a minor claim cites the topical use of aprotinin or another serine peptidase inhibitor with 90% homology to aprotinin for control of the European corn borer (ECB) and Southern corn rootworm (SCR). It was claimed that aprotinin could be used alone or in combination with an insecticidal lectin. Czapla found that incorporation of aprotinin at 20 mg/ml of diet killed 100% of neonatal ECB larvae in a laboratory assay, and killed 60% of neonatal SCR. Ingestion rates as high as these would be difficult to achieve by topical application, and treatment costs would be unlikely to be competitive with chemical insecticides. Czapla found that the serine peptidase inhibitor SBTI (Kunitz and Bowman-Birk) and the cysteine peptidase inhibitor cystatin were less effective than aprotinin.

Direct feeding of SBTI to blood sucking insects has been investigated by Deloach and Spates (1980). They found raised mortality and suppressed egg hatch when SBTI was encapsulated in bovine erythrocytes and used as a bait for horn-fly. Various natural peptidase inhibitors (principally of serine peptidases) are known in blood. However, they have limited efficacy in protecting the animal from insect attack (Sandeman et al, 1990).

Wolfson and Murdock (1987) observed that whilst there is extensive documentation on the presence and distribution of peptidase inhibitors in plants, and these inhibitors are presumed to be targeted at insect digestive peptidases, there is little direct evidence to support their efficient action in inhibiting insect growth and development. These authors demonstrated that larval growth reduction in Colorado potato beetle could be obtained by feeding E-64 (a cysteine peptidase inhibitor) at threshold levels of 50 $\mu$g/ml on potato leaves. However at a much higher application level (1000 $\mu$g/ml) a plateau in mortality of 74–85% was found, which is insufficient for practical use. SBTIs (Kunitz and Bowman-Birk) were ineffective as growth retardants, and there was only a small response to pepstatin.

A research paper by Dymock et al (1992) has discussed the inhibition of growth of a larval coleopteran (New Zealand native grass grub) by peptidase inhibitors. The research was focussed on the genetic transformation of important pasture species, as the grubs feed on roots. Bioassays showed growth inhibition using serine peptidase inhibitors. Some anomalous responses to particular inhibitors were noted (inhibition by SBTI, POT I, POT II, CpTI, stimulation by LBTI). Cristeller et al (1989) had previously identified trypsin as the principal gut peptidase in the above grub, despite the fact that normally coleopteran gut peptidases are predominantly of the cysteine category. Generally the use rate of peptidase inhibitors required to achieve mortality was too high to be cost effective in topical use.

Compositions that function by inhibition of metallopeptidases (including aminopeptidase or LAP) have not been commercially developed for the control of insects. In fact, the prior art teaches away from the use of peptide-based aminopeptidase inhibitors or metallopeptidase inhibitors for insect control, because:

(a) effective inhibitors of the above category suitable for the genetic transformation of plants have not been identified, (b) the apparent role of these enzymes is minor relative to the dominant cysteine and/or serine peptidase activities in the gut of insects.

Shenvi (1993) has discussed the use of $\alpha$-amino boronic acid derivatives as effective inhibitors of mammalian aminopeptidases. Shenvi notes that certain intermediates in the synthesis of $\alpha$-amino boronic acid derivatives have insecticidal properties; however these intermediates did not have an amino group, and are not suggested to act either as aminopeptidase inhibitors or peptidase inhibitors of any sort.

The hexadentate metal chelating agent EDTA has been recognised by Samuels and Paterson (1995) and Ferreira and Terra (1986) to be an inhibitor of an aminopeptidase derived from the moulting fluid and digestive membranes. There is no recognition of any insecticidal effect of EDTA; however general claims for the insecticidal action of metal chelating agents have been made by Tomalia and Wilson (1985, 1986). No supporting evidence was presented. The use of metal chelating agents for insect control would be expected to be adversely influenced by the use of hard water for spray application, or if there was mineral or soil contamination of the materials to be treated.

We have now surprisingly found that compositions comprising an aminopeptidase inhibitor or metallopeptidase inhibitor and further comprising a non-strongly-chelating peptidase inhibitor are able to prevent the hatching of insect eggs and/or the development of insect larvae. The person skilled in the art will recognise that the vast majority of aminopeptidase inhibitors are in fact non-strongly-chelating, as this term is defined herein.

It will be clearly understood that the invention is applicable to the control of insects via a variety of mechanisms. The methods of the invention may, for example, result in the actual killing of insects, or in the interruption of insect growth and development so that maturation is slowed or prevented. Prevention of hatching of insect eggs is particularly desirable, since many economically important insects cause damage as a result of the feeding activities of their larvae.

It will be also understood that because of the wide variation of individual biochemical capacities within members of the class Insecta, responses to particular inhibitors and/or combinations of inhibitors will vary between species. Thus it is possible that some compositions within the scope of this invention will be poorly effective or even ineffective against some insects, while being highly effective against others. Variations in responses may also be seen at subspecies level or at different stages in the life cycle for particular insects, or even with the diet of the insects. Those skilled in the art will be able to match relevant inhibitors to insect targets by application of normal trial and error laboratory and field experimentation.

It will also be apparent to the person skilled in the art that the invention may be utilised in variety of ways, including but not limited to:

(a) control of insect infestation by direct application to a plant or animal vulnerable to such infestation;

(b) reduction of insect numbers by application of the agents of the invention to insect habitat or breeding sites;

(c) control, either by way of prophylaxis or reduction in severity, of infections in plants or animals which are transmitted by insects; and (d) control, by way of prophylaxis or reduction in severity, of infections in plants or animals which are consequential upon insect infestation.

For the purpose of this specification, the term "peptidase inhibitor" is to be understood to be any compound able to inhibit any peptidase.

In practical terms a peptidase inhibitor can be identified by the following process.

1. Select representative active peptidases, which may be purified or in compositions comprising the active enzyme.

2. Select an enzyme activity assay for each of the representative peptidases by selecting an appropriate substrate for the enzyme and conditions for the reaction so as to yield an appropriate quantifiable endpoint in a convenient time.

3. The test compound is considered to be a peptidase inhibitor if a reaction inhibition of 50% or greater is found in any of the above enzyme activity assays.

Specifically, a metallopeptidase inhibitor or an aminopeptidase inhibitor may be identified in this way.

The term "non-strongly-chelating peptidase inhibitor" is to be understood to mean a peptidase inhibitor that chelates $Zn^{2+}$ ions less strongly than EDTA in a competitive binding assessment. Both EDTA and the inhibitor should be at the same concentration in the reaction mixture, which may conveniently be 0.1 mM. The person skilled in the art will be able to choose appropriate reaction conditions and methods for determining $Zn^{2+}$ distribution (eg. using multinuclear nuclear magnetic resonance (NMR), UV spectroscopy, voltametric techniques and soft ionization mass spectroscopy).

SUMMARY OF THE INVENTION

In one aspect, the invention comprises a composition for controlling insects, said composition comprising an aminopeptidase inhibitor or a metallopeptidase inhibitor, and further comprising a non-strongly-chelating peptidase inhibitor.

The aminopeptidase inhibitor or metallopeptidase inhibitor may comprise an amino group or derivative thereof, or one or more amino acid moieties or derivatives thereof. Preferably the aminopeptidase inhibitor or metallopeptidase inhibitor comprises a leucine, arginine, methionine, aspartic, alanine, glutamyl, prolyl, valyl or cysteine moiety or derivative thereof. More preferably the aminopeptidase inhibitor or metallopeptidase inhibitor comprises a leucine moiety or derivative thereof.

The aminopeptidase inhibitor or metallopeptidase inhibitor may interact with metal ion(s) in the active site of the metallopeptidase or aminopeptidase.

The aminopeptidase inhibitor or metallopeptidase inhibitor may comprise a chelating agent, which is preferably a bidentate, tridentate, quadridentate or hexadentate chelating agent. Preferably the chelating agent is an amino carboxylic acid moiety or salt thereof having chelating action, and more preferably is ethylene diaminetetraacetic acid, or is nitrilo triacetic acid or a salt or derivative thereof having chelating action.

The aminopeptidase inhibitor or metallopeptidase inhibitor may comprise a water soluble transition metal ion or complex or derivative selected from the group consisting of copper, cobalt, zinc, vanadium, magnesium, manganese and iron.

The aminopeptidase inhibitor or metallopeptidase inhibitor may comprise a boronic, phosphoryl or phosphonyl moiety.

The aminopeptidase inhibitor or metallopeptidase inhibitor may bind irreversibly to an aminopeptidase or metallopeptidase.

The aminopeptidase inhibitor or metallopeptidase inhibitor may comprise a selective inhibitor which does not inhibit trypsin or calpain, and which preferably does not inhibit other serine or cysteine peptidases.

The aminopeptidase inhibitor or metallopeptidase inhibitor may inhibit an enzyme selected from the group consisting of leucine aminopeptidases, aminopeptidases of type A, B, N and M, arginine aminopeptidases, methionine aminopeptidases, D-amino acid aminopeptidases, peptidyl dipeptidases, zinc aminopeptidases, N-formyl methionine aminopeptidases, dipeptidyl-aminopeptidases, carboxypeptidases of type A and B, tripeptidyl peptidases, dipeptidyl peptidases and peptidyl-tripeptidases.

Preferably the aminopeptidase inhibitor or metallopeptidase inhibitor is capable of inhibiting a leucine aminopeptidase and more preferably inhibits an insect leucine aminopeptidase.

The non-strongly-chelating peptidase inhibitor may comprise a serine peptidase inhibitor, a cysteine peptidase inhibitor, an aspartyl peptidase inhibitor, or an aminopeptidase inhibitor. Inhibitors suitable for use in the invention include but are not limited to trypsin and chymotrypsin inhibitors, such as 4-(2-aminoethyl)-benzenesulfonylfluoride hydrochloride (PEFABLOC)

serine or cysteine peptidase inhibitors derived from legumes, vegetables, fruits or cereals;

cystatins and E-64;

carboxypeptidase inhibitors from potato or other sources;

Eglin C;

L-leucinethiol.

Trypsin and chymotrypsin inhibitors include but are not limited to Kunitz trypsin inhibitor (SBTI), Bowman-Birk trypsin and chymotrypsin inhibitor, soya bean trypsin inhibitor, bovine pancreatic trypsin inhibitor, chicken ovomucoid trypsin inhibitor, *Cucurbit maxima* trypsin inhibitor, POT-I and POT-II trypsin inhibitor, alpha-1-antitrypsin, arrowhead trypsin inhibitor, erythrine trypsin inhibitor, and human inter-alpha trypsin inhibitor.

Serine or cysteine peptidase inhibitors derived from legumes, vegetables, fruits or cereals include but are not limited to peptidase inhibitors from red bean, cowpea, split pea, wing bean, mung bean, mustard, squash, caraway, cajun pea, cotton, corn, wheat, sorghum, rapeseed, millet, barley and pumpkin.

Cystatins include but are not limited to oryzacystatin I and II from rice, potato multicystatin and its trypsin digested sub-units, and hen egg cystatin.

In each instance herein where reference is made to peptidase inhibitors by common name, the reference is intended to include analogues of these inhibitors, ie. inhibitors with similar structure and/or inhibitory characteristics (interactions with the target enzyme active site(s)) to the commonly recognised substance(s).

Appropriate analogues may be portions of the named inhibitor, conjugates thereof, or substances with at least 70% homology, preferably at least 80% homology, and more preferably at least 90% homology to the named substance.

The composition of the invention may optionally also comprise one or more additives such as dispersant, viscosity modifiers, anti-freeze agents, wetters, cosolvents, UV absorbers, dyes and carriers which are acceptable for pharmaceutical, veterinary, agricultural or horticultural use.

In one embodiment, the composition of the invention comprises an aminopeptidase inhibitor selected from the group consisting of L-leucinethiol, actinonin, bestatin, 1,10-phenanthroline and EDTA, together with a non-strongly-chelating peptide inhibitor selected from the group consisting of SBTI, pefabloc and antipain.

The aminopeptidase inhibitor or metallopeptidase inhibitor or non-strongly-chelating peptidase inhibitor preferably comprises a peptide, polypeptide and/or protein.

In a second aspect, the invention provides a method for controlling insects, comprising the step of exposing said insects to a composition according to the invention.

Preferably the insects are controlled by inhibiting the hatching of insect eggs and/or inhibiting the development of insect larvae by exposing said insect eggs or larvae to a composition of the invention.

Preferably the insect is a species of an order selected from the group consisting of Lepidoptera, Hemiptera, Orthoptera, Coleoptera, Psocoptera, Hymenoptera, Dictyoptera, Isoptera, Thysanoptera, Homoptera, Diptera, Anaplura, Malophaga and Siphonaptera. More preferably the insect is selected from the group consisting of myiasis flies, Budworms, fleas, field crickets, cockroaches, light brown apple moth and insects that infest stored grain or grain products.

According to the method of the invention, the target insect may be exposed to the enzyme inhibitor by any suitable means. A person skilled in the art will appreciate that these means may vary widely, depending upon whether the inhibitor is to be applied to a plant or animal, and depending on the nature of the target insect and of the plant or animal. The means suitable for applying enzyme inhibitors directly to a plant or animal which is attacked by the insect may differ considerably from means suitable for applying the enzyme inhibitor to insect habitat or breeding sites.

Suitable means of application of enzyme inhibitors to animals include but are not limited to direct topical application, such as by dipping or spraying, or internal application such as oral drenching, implants, delayed release bolus formulations or devices adapted for retention in the rumen and insect baits and tablets. Where the agents of the invention are to be applied to humans, formulations suitable for topical application include but are not limited to sprays, aerosols, creams and lotions, and formulations suitable for internal application include but are not limited to tablets, capsules or liquid formulations. In some situations parenteral administration by injection may be the most suitable means of treatment for humans or animals.

Where the enzyme inhibitor is to be applied to plants, suitable means include but are not limited to sprays, dusts, pellets, or aerosols. The method of the invention also encompasses the concurrent or successive use of two or more metallopeptidase inhibitors, or the use of one or more metallopeptidase or aminopeptidase inhibitors in conjunction concurrently or successively with one or more inhibitors of other types of enzymes, one or more inhibitors of other insect physiological processes, or one or more other insecticidal agents whether these other inhibitors are delivered topically, internally or through transgenic modification.

Some inhibitors useful for the purposes of the invention are peptide, polypeptide or protein in nature. Where this is the case, either or both of the aminopeptidase or metallopeptidase inhibitors and the non-strongly-chelating peptidase inhibitor may be supplied by transgenic expression in or in association with the target plant or non-human animal to be treated. Where only one of these inhibitors is expressed transgenically, the other may be supplied by topical application.

The transgenic organism is preferably a plant or non-human animal vulnerable to attack by an insect, but may also be an organism which is resident in or on an animal or plant which is vulnerable to such attack. In the latter case, the organism is preferably symbiotic or commensal with the plant or animal. Suitable resident organisms include, but are not limited to Bacillus species or Pseudomonas species, or Mycobacterium species. In a preferred embodiment, the organisms are *Bacillus thuringiensis* or *Mycobacterium phlei*. Methods for producing transgenic organisms are well known in the art, and plants which express *Bacillus thuringiensis* crystal protein show some resistance to insect attack.

In preferred non-limiting embodiments of the invention:

(a) The animals treated by the methods of the invention are selected from the group consisting of humans, sheep, cattle, horses, pigs, poultry, dogs and cats.

(b) The plants treated by the methods of the invention are selected from the group consisting of cotton, oil seed crops, ornamental plants, flowers, fruit trees, cereal crops, vine crops, root crops, pasture plants and vegetables.

(c) The insects to be controlled in the case of horticultural and broadacre applications of the invention are Lepidoptera, Hemiptera, Orthoptera, Coleoptera, Isoptera, Thysanoptera or Homoptera, in the case of insect infections in animals are Diptera, Anaplura, Malophaga or Siphonaptera, or in the case of domestic or industrial pests are Isoptera, Dictyoptera and Hymenoptera.

(d) The transgenic plants are selected from the group consisting of cotton, oil seed crops, ornamental plants, flowers, fruit trees, cereal crops, vine crops, root crops, pasture plants, and vegetables, and (e) The transgenic organisms to be resident in or on an animal or plant are *Bacillus sp* or *Pseudomonas sp* or *Mycobacteria sp*.

The transgenic plants or organisms may be prepared in accordance with techniques know to persons skilled in the art. For example, a non-human animal or plant or organism may be modified by the steps of:

Preparing a suitable vector comprising a nucleotide sequence that codes for a peptide agent that inhibits an aminopeptidase or "non-strongly-chelating" peptidase and a promotor wherein the nucleotide sequence is capable of being expressed by a host contained the vector.

Incorporating the vector into the host; and

Maintaining the host containing the vector under conditions suitable for transcription and translation of the nucleotide sequence into said peptide agent.

DETAILED DESCRIPTION OF THE INVENTION

The invention will now be described in detailed by way of reference only to the following non-limiting examples.

The following examples demonstrate insect growth inhibition or insecticidal activities obtained by use of the invention. It will be understood however that other methods and applications can also be employed. Effects of inhibitors of serine and cystine peptidases alone (not within the field of this invention) are included to illustrate variability in responses to inhibitors between species, or to exemplify additive or synergistic benefits subsequently obtained through use of the invention.

EXAMPLE 1

Influence of Individual Inhibitors on Growth and Survival of Larvae of Sheep Blowfly (Lucilia cuprina; Diptera)

Method

Larvae were hatched from eggs that had been surface sterilised with 0.5% sodium hypochlorite and incubated overnight at 27° C. The first instar larvae were collected and placed onto 1 ml of an autoclaved culture medium with or without added inhibitor(s), as designated. The culture medium consisted of 2% agar, 10% casein, 2% yeast and 0.5% glucose in distilled water in a sterile vial or bottle. Five to fifty larvae, depending on the intended duration of the culture, were placed in each bottle, which was then capped using a lid with a fine plastic mesh insert. This cap allowed free exchange of air into the bottle.

The bottles were then placed inside a large sterile container which was sealed to prevent contact with the environment. The container included inlet and outlet tubes connected to a source of sterile warmed humidified air and a vacuum pump, respectively. The apparatus, including culture bottles, was kept at 35° C. for 24 to 72 hours. This allowed growth of the larvae to required development stages.

Cultures were set up in a sterile air flow hood and incubated in a sterile environment to minimise likelihood of contamination by bacteria that may assist or hinder larval growth thereby invalidating results. After the intended culture period, the bottles were removed and the larvae killed by freezing. They were then dried and weighed, wither collectively or individually.

The weight of insect larvae in control cultures (larvae grown concurrently, under the same environmental conditions and food—except without inhibitors) were then compared to those which included inhibitors and the percent inhibition (I) calculated according to the formula:

$$I = \frac{c-a}{c} \times 100$$

where a=the weight of larvae in the presence of the inhibitor and c=the weight of control larvae.

A large number of inhibitors has been tested in this culture system, and a selection of these is listed in Table 1.1. The effects of inhibitors on first instar larval growth and survival are shown in Table 1.2

TABLE 1.1

Peptide inhibitors and related compounds tested against blowfly larvae in vitro

| Inhibitor | Peptidase types affected | Special conditions* |
|---|---|---|
| Soybean Trypsin Inhibitor (SBTI) | Serine | |
| AEBSP (4-(2-aminoethyl)-benzenesulfonyl fluoride, hydrochloride) (=Pefabloc) | Serine | |
| APMSF ((p-amidinophenyl) methane sulfonyl fluoride | Serine & cysteine | Soluble in DMSO |
| E64 (L-trans-epoxysuccinyl leucylamido (4-guanidino | Cysteine | |
| Leupeptin (Ac-Leu-Leu-Arginyl.1/2H$_2$SO$_4$H$_2$O) | Serine & cysteine | |
| TPCK (Tos-Phe-CH$_2$Cl, tosyl chloromethyl-ketone) | Serine (Chymotrypsin-like) | Soluble in MeOH |
| TLCK (Tos-Leu-CH$_2$Cl, tosyl chloromethyl ketone | Serine (Trypsin-like) | |
| Calpain inhibitor I (N-Acetyl-Leu-Ley-norleucinal) | Calcium-activated cysteine peptidases | Soluble in MeOH |
| L-leucinethiol (2-amino-4-methyl-1-pentanethiol) | Aminopeptidases | |
| Bestatin (2S,3R)-3-amino-2-hydroxy-4-phenyl-butanoly)-Leu-OH) | Aminopeptidases | Soluble |
| Leuhistin ((2R,3S)-3-amino-2-hydroxy-2-(lII-imidazole-4-methyl)-5-methylhexanoic acid | Aminopeptidases | Soluble in MeOH |
| Amastatin (((2S,3R)-3-amino-2-hydroxy-5-methyl-hexanoyl)-Val-Val-Asp-OH | Aminopeptidases | Soluble in MeOH |
| Diprotin A (H-Ile-Pro-Ile-OH) | Dipeptidyl aminopeptidases | |
| Ebelactone B (3,11-dihydroxyl-2,4,6,8,10,12-hexa-methyl-9-oxo-6-tetra-decenoic 1,3-lactone | N-formyl-methionine aminopeptidases | Soluble in MeOH |
| Actinonin (3-((1-((2-(hydroxymethyl)-1-propyl-idinyl)-carbonyl)-2-methylpropyl)-(carbamoyl)-octanohydroxamic acid) | Aminopeptidases | Soluble in MeOH |
| EDTA (ethylene-diamine-tetra-acetic acid disodium salto | Metallo (general) | |
| Pepstatin | Aspartic | |
| Antipain | Aminopeptidases Metallopeptidases | soluble in MeOH | unless otherwise stated, enzyme inhibitors are soluble in sterile phosphate buffered saline or water. Those which are only soluble in DMSO/H2O or MeOH/H2O were compared to control treatments which included the same amounts of DMSO or MeOH.

TABLE 1.2

The effects of various inhibitors on first instar larval growth and survival

| Inhibitor | Concentrations Tested (mM) | Growth Inhibition |
|---|---|---|
| SBTI | 0.17, 0.20, 0.40, 1 | 76% inhibition at 0.17 mM<br>64% inhibition at 0.40 mM |
| PEFABLOC | 0.5, 1, 10, 25, 50 | 72% inhibition at 10 mM<br>92% inhibition at 50 mM |
| APMSF | 1, 2, 5 | 43% inhibition at 5 mM |
| E64 | 1, 2, 5 | No inhibition detected |
| EDTA | 1, 2.5, 5, 10 | 84% inhibition at 5 mM<br>All killed at 10 mM |
| L-leucinethiol | 1, 2, 5 | 47% inhibition at 2 mM<br>All killed at 5 mM |
| Bestatin | 1, 2.5, 5 | 63% inhibition at 5 mM |

TABLE 1.2-continued

The effects of various inhibitors on first instar larval growth and survival

| Inhibitor | Concentrations Tested (mM) | Growth Inhibition |
|---|---|---|
| Leupeptin | 1, 2, 5, 10 | 71% inhibition at 2 mM |
|  |  | 80% inhibition at 10 mM |
| TLCK | 1, 2.5, 5, 10 | All killed at 5 and 10 mM |
| TPCK | 1, 2, 5, 10 | No inhibition detected |
| Calpain inhibitor I | 1, 2, 5 | 71% inhibition at 2 mM |
| Leuhistin | 1, 2, 5 | 65% inhibition at 5 mM |
| Amastatin | 1, 2, 5 | 90% inhibition at 10 mM |
|  |  | 60% inhibition at 2 mM |
| Diprotin | 1, 2, 5, 10 | No inhibition detected |
| Ebelactone B | 1, 2, 5 | 18% inhibition at 2 mM |
| Actinonin | 1, 2.5, 10 | 95% inhibition at 10 mM |
|  |  | 83% inhibition at 2.5 mM |
| Pepstatin | 1, 2, 10 | No inhibition detected |
| Antipain | 0.3125, 0.625, 1.25, 2.5, 5 | 63.2 at 5 mM |
|  |  | 45.5 at 2.5 mM |
| 1,10-phenanthroline | 1, 2.5, 5 | All larvae died |

Our results indicated that inhibitors which affect trypsin-like enzymes are effective in slowing larval growth, or in the case of TLCK, killing the larvae at the highest concentrations tested. E64, a cysteine peptidase inhibitor, was ineffective; however, the effects of calpain inhibitor on growth and the intermediate inhibition by leupeptin and APMS (not cysteine specific inhibitors) suggest that there may be some essential role for cysteine peptidases.

The ineffectiveness of inhibition of aspartyl peptidase(s) by pepstatin is consistent with prior literature.

The surprising result of this experiment was the dominant influence of some aminopeptidase inhibitors on larval growth. These results indicated that inhibition of larval aminopeptidase(s) was effective. L-leucinethiol, EDTA, 1,10-phenanthroline, bestatin, amastatin, leuhistin, and actinonin were effective growth inhibitors. Inhibitors of dipeptidylamino peptidase (Diprotin A) and methionine aminopeptidase (Ebalactone) were ineffective.

EXAMPLE 2

Influence of combined peptidase inhibitors on growth and survival of larvae of sheep blowfly (L. cuprina; Diptera)

(a) Use of combined serine and serine:aminopeptidase inhibitor combinations.

The data from tests outlined in Example 1 suggested that combinations of inhibitors which affected trypsin-like and/or aminopeptidase enzymes might have additive or synergistic effects. Further experiments were carried out to examine this possibility using methods previously described. The results are shown in Table 2.1.

TABLE 2.1

Inhibitor combinations and their effects on first instar larval growth and survival in vitro

| Inhibitor | Concentrations Tested (mM) | Growth Inhibition |
|---|---|---|
| SBTI + Pefabloc | 0.17 SBTI + 2.5 Pefabloc | 72% inhibition of growth |
| SBTI + TLCK | 0.17 SBTI + 2.5 TLCK | Larave killed |
| SBTI + Leupeptin | 0.17 SBTI + 2 Leupeptin | 44% inhibition of growth |
| SBTI + L-leucinethiol | 0.17 SBTI + 0.5, 0.75 or 1 L-leucinethiol | Larvae killed at all concentrations |
| SBTI + EDTA | 0.17 SBTI + 2 or 5 EDTA | 5 mM: 92% growth inhibition |
|  |  | 2 mM: 88% growth inhibition |
| SBTI + Bestatin | 0.17 SBTI & 3.3 Bestatin | 73% inhibition of growth |
| EDTA + PEFABLOC | 1.0 EDTA + 3.0 Pefabloc | 78% inhibition of growth |
| EDTA + Antipain | 0.5 EDTA + 5.0 Antipain | 85% inhibition of growth |

Little effect was apparent from combining SBTI and leupeptin or Pefabloc. A moderate effect was obtained with SBTI and EDTA. Greater inhibition occurred when SBTI was tested with TLCK or L-leucinethiol. The results suggested that multiple inhibition of trypsin-like peptidases and aminopeptidases has a useful inhibitory effect on the larvae.

(b) Investigation of the effect of combining a serine peptidase inhibitor (SBTI) with an aminopeptidase inhibitor (L-leucinethiol) on growth inhibition of larval L. cuprina The effect on larval growth of combined SBTI and L-leucinethiol inhibitors was investigated over a range of concentrations to investigate the possibility of a synergistic inhibition occurring. This experiment was terminated prior to significant mortality. The results are shown in Table 2.2.

TABLE 2.2

The effect of larval growth inhibition of a combination of SBTI and L-leucinethiol (L-leu) inhibitors

| Inhibitor(s) | Concentration (mM) | Average Larval Weight ($10^{-4}$ g) | % Growth Inhibition |
|---|---|---|---|
| Control | — | 10.26 | — |
| SBTI | 0.0425 | 12.57 | -22.5 |
| SBTI | 0.085 | 7.34 | 28.5 |
| SBTI | 0.170 | 5.63 | 45.1 |
| SBTI | 0.340 | 3.15 | 69.3 |
| SBTI | 0.680 | 3.02 | 70.6 |
| L-leu | 1.00 | 8.06 | 21.4 |
| L-leu | 2.00 | 2.76 | 73.1 |
| SBTI & L-leu | 0.02175 & 0.5 | 11.90 | -15.9 |
| SBTI & L-leu | 0.0425 & 0.5 | 6.77 | 34.0* |
| SBTI & L-leu | 0.085 & 1.0 | 2.90 | 71.7* |
| SBTI & L-leu | 0.17 & 1.0 | 2.41 | 76.5* |
| SBTI & L-leu | 0.34 & 1.0 | 0.99 | 90.5* |

*These combined responses confirm synergy as defined by Cornell (1981, p.24)

(c) Investigation of the effect of combining two aminopeptidase inhibitors (EDTA and L-leucinethiol) on growth of larval L. cuprina The results of these experiments are shown in Table 2.3

TABLE 2.3

Combination of EDTA and L-leu

| Treatment | Concentration (mM) | Average Larval Weight ($10^{-4}$ g) | % Growth Incubation |
|---|---|---|---|
| Control | — | 9.08 | — |
| EDTA | 0.25 | 9.68 | -6.6 |
| EDTA | 0.50 | 5.47 | 39.8 |

TABLE 2.3-continued

Combination of EDTA and L-leu

| Treatment | Concentration (mM) | Average Larval Weight ($10^{-4}$ g) | % Growth Incubation |
|---|---|---|---|
| EDTA | 1.0 | 2.75 | 69.7 |
| EDTA | 1.5 | 4.43 | 51.2 |
| EDTA | 2.0 | 2.51 | 72.4 |
| L-leu | 1.0 | 2.98 | 67.2 |
| L-leu | 2.0 | 1.22 | 86.6 |
| EDTA & L-leu | 0.15 & 0.50 | 8.66 | 4.6 |
| EDTA & L-leu | 0.25 & 0.50 | 5.56 | 38.6 |
| EDTA & L-leu | 0.50 & 0.50 | 3.94 | 56.6 |
| EDTA & L-leu | 0.75 & 0.50 | 3.65 | 59.8 |
| EDTA & L-leu | 1.00 & 1.00 | 2.94 | 67.6 |

EXAMPLE 3
Influence of Peptidase Inhibitors on Egg Hatch of Larvae of Sheep Blowfly (*L. cuprina*; Diptera) and *Heliothis punctigens*

The following experiments were conducted to assess whether the compositions of invention could fulfil an insecticidal role through an inhibition of egg hatching.

*L. cuprina* eggs were placed on pieces of liver (0.9 g) which were then placed in individual wells of a 24-well tissue culture plate. Phosphate buffered saline (PBS, 0.1 ml) containing inhibitors at set concentrations were added to each well with 30 freshly laid and sterilised eggs of *L. cuprina*. The culture plate was then maintained in a sterile environment at 35° C. for 24 hours, after which time the percentage hatch was assessed.

Heliothis eggs were cultured on a defined medium (casein 3 g, wheatgerm 3 g, sucrose 5 g, agar 2.25 g, multivitamin B tablets 5 mg, dissolved in 80 ml PBS with penicillin and streptomycin) in 24-well tissue culture plates (2 eggs/well). Egg hatch was assessed after 3 days incubation at 27° C. The results are shown in Table 3.1

TABLE 3.1

The Effect of Enzyme Inhibitors on Egg Hatch Rates for *L. cuprina* in vitro

| Inhibitors | Concentrations (mM) | % Hatch |
|---|---|---|
| Control | | 71 |
| EDTA | 2, 5, 10 | 10, 0 10 |
| Soybean trypsin inhibitor | 0.17 | 17 |
| Soybean trypsin inhibitor + EDTA | 0.17 SBTI + 2, 5, 10 EDTA | 15, 25, 7 |
| TLCK + EDTA | 2, 5, 10 TLCK + 2 EDTA | 3, 7, 2 |

In initial in vitro trials, ten Heliothis eggs did not hatch in a mixture of 0.17 mM SBTI and 5 mM Actinonin while all ten control eggs hatched.

EXAMPLE 4
Influence of the Invention on Growth and Survival of Cotton Budworm (*Heliothis punctigens*, Lepidoptera) Larvae Fed an Artifical Diet.

An artificial diet was prepared as follows:

| Haricot Beans | 466 gram (g) |
|---|---|
| Wheat Germ | 100 g |

-continued

| Yeast | 70 g |
|---|---|
| Ascorbic Acid | 70 g |
| Paraben | 44 g |
| Sorbic Acid | 2.2 g |
| Agar | 28 g |
| $H_2O$ | 800 ml |
| *Phosphoric and propionic Acid | 4 ml |

*Stock solution of phosphoric and propionic acid contained
| | 29 ml | Propionic Acid |
|---|---|---|
| | 21 ml | Orthophosphoric Acid |
| | 270 ml | $dH_2O$ |
| Total vol. | 500 ml | |

1. The Haricot beans were cooked in a microwave for 40 minutes.
2. Agar was added to the hot water and stirred on a hot plate until almost boiling.
3. The haricot beans, agar mix, yeast and wheat germ was blended in an electric mixer for 3 minutes.
4. When the temperature has dropped to 60°C., the acids were added and mixed with the media.
5. Inhibitor solutions or an equal volume of water were placed into sterilized glass tubes at designated concentrations. The artificial media was added to each tube (1.5 ml) using a sterile 10 ml syringe. First instar *Heliothis punctigens* larvae (1 larvae per tube) were added to the glass tubes and the tubes were capped. The tubes were incubated for 10 days at 25° C. The larvae were killed by placing the glass tubes at −70° C. for 24 hours, and then individually weighed. Percentage inhibition was calculated by comparison to control larvae.

The results are shown in Table 4.1

TABLE 4.1

Growth of *Heliothis punctigens* Larvae Fed an Artificial Diet With and Without Inhibitors

| Inhibitor | Concentration (mM) | % Alive | Average Laval Weight (mg) | % Growth Inhibition |
|---|---|---|---|---|
| Control | — | 70.0 | 165.4 | — |
| Carboxypeptidase Inh. | 2.5 | 83.3 | 140.6 | 15.0 |
| Carboxypeptidase Inh. | 5.0 | 50.0 | 123.6 | −53.5 |
| EDTA | 2.5 | 50.0 | 123.6 | 25.3 |
| EDTA | 5.0 | 33.3 | 9.25 | 94.4 |
| EDTA | 10.0 | 67.0 | 4.75 | 97.1 |
| Leupeptin | 2.5 | 16.6 | 16.6 | 90.0 |
| Leupeptin | 5.0 | 33.3 | 17.0 | 89.7 |
| Actinonin | 2.5 | 33.3 | — | 97.5 |
| Actinonin | 5.0 | 0.00 | — | 100.0 |
| EDTA & SBTI | 2.5 & 0.17 | 75.0 | 22.0 | 86.7 |
| EDTA & SBTI | 5.0 & 0.17 | 25.0 | 5.00 | 97.0 |

EXAMPLE 5
Influence of Peptidase Inhibitors on Growth and Survival of Cat Fleas (*Ctenocephalides felis*; Siphonaptera)

Blood was collected from the jugular vein of a five year old merino sheep that had not been treated with an ectoparasitic agent for 18 months. The blood was collected into a 100 ml plastic bottle containing 0.8 ml of heparin and was maintained at 4° C. Inhibitors were pre-weighed into sterile 5 ml plastic vials and 4.5 ml of blood added. The samples were mixed, placed at −70° C. for 24 hours, then freeze-dried. The freeze-dried samples were sieved through a stainless steel 63 micron sieve, and placed into sterile 5 ml plastic vials (0.15 g/per tube). Four flea eggs were placed into each vial, and a sheet of tissue paper fastened by an elastic band was fitted to the top of each vial. The vials were incubated at 25° C. and 70–80% R H for 6 days. Vermiculite was then added to each vial to provide a supporting medium for the fleas to pupate and the tubes incubated at 25° C. and 70–80% R H, for a further 10 days. Ten control vials and three vials of each treatment were tested.

At the conclusion of the incubation period the vials were placed at −20° C. for 24 hours to kill the fleas. The number of eggs hatched and the life-cycle state was recorded. The results are shown in Table 5.1.

TABLE 5.1

Development of Flea eggs in Dried Blood Diets (Day 16)

| Treatment | | Percentage of Fleas Progressing Through to Pupation |
|---|---|---|
| Control | | 97.5 |
| EDTA | 1.5625 mg | 0 |
| | 3.125 mg | 0 |
| | 6.25 mg | 0 |
| Actinonin | 1.40 mg | 0 |
| | 2.80 mg | 16.8 |
| Leupeptin | 1.70 mg | 0 |
| | 3.40 mg | 0 |
| SBTI | 5.0 mg | 0 |
| | 10.0 mg | 0 |
| PEFABLOC | 1.10 mg | 0 |
| | 2.20 mg | 0 |
| EDTA & SBTI | 1.5625 mg 5 mg | 0 |
| EDTA & SBTI | 3.125 mg 5 mg | 0 |

EXAMPLE 6

Influence of Peptidase Inhibitors on Survival of Larvae of the Black Field Cricket (*Teleogryllus commodus*, Orthoptera) Fed a Natural Diet.

(i) Stock solutions of inhibitors and control solutions were prepared as aqueous solutions or suspensions as outlined in Table 6.1.

(ii) Mortality was assessed by commencing the study with 1st instar nymphs.

(iii) Cabbage leaf disks (5×8 mm diameter disks/treatment) were smeared with 100 µl of inhibitor or control stock solutions and allowed to dry. Disks were placed singly in 40 mm petri dishes, together with a moist cotton wool pas as water supply and a piece of fluted plastic for shelter.

(iv) Ten nymphs were placed on each disc and the dishes incubated at 25° C.

(v) Mortality was assessed daily and any dead individuals removed.

The results are shown in Table 6.1

TABLE 6.1

Effect of Various Inhibitors on Mortality of Larval Field Crickets After 7 days

| Inhibitor | Concentration Range Tested (mM) | Mortality |
|---|---|---|
| Actinonin | 5 | None |
| EDTA | 30 | High (78%) |
| SBTI | 0.17–0.68 | None |
| EDTA/SBTI | additive of B & C above | High (41%) |
| PEFABLOC | 2.5–10 | Medium |
| 1,10-phenanthroline | 5–20 | Medium |

TABLE 6.1-continued

Effect of Various Inhibitors on Mortality of Larval Field Crickets After 7 days

| Inhibitor | Concentration Range Tested (mM) | Mortality |
|---|---|---|
| Actinonin/SBTI | additive of A & C above | Low |
| Antipain | 2.5–10 | None |
| Borax | 5–20 | High (93%) |
| Control (water) | — | — |

*none/low, 10–20% mortality/medium 21–40%/high 41–100%.

EXAMPLE 7

Influence of Peptidase Inhibitors on Growth and Survival of Sheep Lice (*Bovicola ovis*; Anoplura)

Sheep lice are a major agricultural insect pest in Australia and many other countries. Some strains of the insects are developing high levels of resistance to organophosphates and synthetic pyrethroids. This trial was conducted to:

(i) broaden the assessment of growth inhibition or insecticidal activity of the inhibitors useful in the inveniton; and (ii) to assess the growth inhibition or insecticidal activity of the invention on a strain of insect with a known high level of insecticide resistance.

The strain of lice chosen was a reference strain known as Hartley. It is highly resistant to synthetic pyrethroids (Table 7.1, Levot G. W., Aust. Vet. J., 1992 69 120).

(i) Lice were collected by clipping a small area of wool from a heavily infected sheep and covering the shorn area for 1 minute with cotton cloth. Lice were brushed from the cloth into a container.

(ii) Aqueous stock solutions or suspensions of inhibitors were applied to tufts of wool taken from the 40 mm of fleece closest to the skin. The donor sheep was known not to have been treated with insecticide for 2 years, and its wool had a staple length of 100 mm at shearing.

(iii) Taking care to avoid cross contamination, quadruplicate wool samples were treated by immersion in aqueous solutions or suspensions of inhibitors, drained and air dried for 24 h.

(v) The wool samples were added to labelled, capped plastic tubes.

(v) Lice were allowed to crawl across paper away from a light source (as a viability test) and 10 lice from each of adult, 3rd, 2nd and 1st instar added to each tube of wool.

(vi) Tubes were incubated at 35° C. and 60–80% RH and inspected daily.

(vii) Viability assessments were made by assuming lice unable to move when touched were dead.

The results are shown in Table 7.1

TABLE 7.1

Number of Living Lice Grown on Inhibitor Treated Wool After 24 Hours Incubation at 35° C.

| Treatment | | Louse Instar Stage | | | |
|---|---|---|---|---|---|
| (concentration in mM) | | 1 | 2 | 3 | Adult |
| Water | replicate 1 | 10 | 10 | 10 | 10 |
| | replicate 2 | 10 | 10 | 10 | 10 |

TABLE 7.1-continued

Number of Living Lice Grown on Inhibitor Treated
Wool After 24 Hours Incubation at 35° C.

| Treatment | | Louse Instar Stage | | | |
|---|---|---|---|---|---|
| (concentration in mM) | | 1 | 2 | 3 | Adult |
| | replicate 3 | 10 | 10 | 10 | 10 |
| EDTA | 10 | 0 | 2 | 1 | 2 |
| | 20 | 0 | 1 | 0 | 1 |
| | | 0 | 0 | 0 | 0 |
| SBTI | 0.17 | 1 | 2 | 2 | 4 |
| | 0.34 | 1 | 0 | 4 | 0 |
| | 0.68 | 0 | 0 | 0 | 0 |
| EDTA/SBTI | 10/0.17 | 0 | 0 | 0 | 0 |
| | 20/0.34 | 0 | 0 | 0 | 0 |
| | 30/0.68 | 0 | 0 | 0 | 0 |

TABLE 7.2

Insectidial Resistance Characteristics of the Lice Tested

| Insecticide | LC50 (mg/L) | LC95 (mg/L) | Resistance Factor |
|---|---|---|---|
| Cypermethrin | 29.4 | 475 | 642 (Peak Hill) |
| Diatinon | 5.31 | 19.7 | 1.4 (Singapore) |

The composition of the invention was highly effective on insecticide-resistant sheep lice.

EXAMPLE 8
Influence of Peptidase Inhibitors on Growth and Survival of the Bruchid (*Tribolium castaneum*; Coleoptera)

Insects were cultured in cleaned, ground and sieved wholemeal flour made from organic wheat. Inhibitors from bottles of pre-weighed material were dry-mixed with the flour and residual inhibitor rinsed from bottles with a small volume of water. Rinse water was added to the flour and the mixture re-ground. The impregnated flour was transferred to a 20 mL vial and mixed thoroughly by shaking and inverting.

Adults of *T. castaneum* were allowed to oviposit on flour, eggs were sifted from the flour and transferred one by one with a single hair to microwell tubes containing a small amount of flour. Each level of treatment was performed in triplicated using 32 wells/replicate. Assays were performed in triplicated. Cultures were incubated at 30° C. and 55% R H.

After 6 days each replicate of 32 wells was combined, the larvae counted and the numbers compared with numbers in the control (no inhibitor) treatment. Larvae were classified as "small" if appreciably smaller than reference larvae, or abnormal if unusual behaviour or formation were observed (eg. twisting or twisted larvae).

Test inhibitors and dose rates were the same as those used in Example 4.

Results (Day 6)

Egg hatch was not consistently affected at day 6
larvae were classed as "small" at all dose levels of actinonin and EDTA, but were normal in 1,10-phenanthroline and other treatments

EXAMPLE 9
Influence of Peptidase Inhibitors on Growth and Survival of the Grain Storage Pest *Oryzaephylus surinamensis*; Coleoptera)

The bioassay for this insect was outlined for *T. castaneum*, except incubations were conducted at 32.5° C. and 70% R H. After 8 days the insects were sieved from the flour and weighed.

These results are shown in Table 9.1.

TABLE 9.1

Percentage Reduction in Weight of *O. surinamensis* Larvae

| Treatment | Concentration (mM) | Percentage Growth Inhibition* |
|---|---|---|
| Bestatin | 1.25 | −5 |
| | 2.5 | 2 |
| | 5 | −4 |
| EDTA | 10 | 32 |
| | 20 | 4 |
| | 30 | 28 |
| SBTI | 0.17 | 12 |
| | 0.34 | 30 |
| | 0.68 | 46 |
| EDTA/SBTI | 10/0.17 | 63 |
| (additive of above) | 20/0.34 | 30 |
| | 30/0.68 | 44 |
| PEFABLOC | 2.5 | 49 |
| | 5 | 61 |
| | 10 | 79 |
| 1,10-phenanthroline | 5 | 100 |
| | 10 | 63 |
| | 20 | 95 |
| Bestatin/SBTI | 1.25/0.17 | −2 |
| (additive of above) | 2.5/0.34 | 30 |
| | 5/0.68 | 32 |
| Antipain | 2.5 | −10 |
| | 5 | −2 |
| | 10 | −2 |
| Casein | 10 mg/ml | −5 |
| | 20 mg/ml | 10 |
| | 40 mg/ml | −2 |
| Borax | 5 | −5 |
| | 10 | 39 |
| | 20 | 68 |

*Relative to growth in untreated larvae.

The response to individual aminopeptidase inhibitors was variable. 1,10-phenanthroline was a highly effective growth inhibitor, EDTA was moderately effective and bestatin was ineffective.

It will be apparent to the person skilled in the art that while the invention has been described in some detail for the purposes of clarity and understanding, various modifications and alterations to the embodiments and methods described herein may be made without departing from the scope of the invention concept disclosed in this specification.

References cited herein are listed on the following pages, and are incorporated herein by this reference.

REFERENCES

Ahmad Z., Saleemuddin M. and Siddigi
   Insect Biochemistry 1976 6 501–505.
Ahmad Z., Saleemuddin M. and Siddigi
   Insect Biochemistry 1980 10 667–673.
Anon
   In: The Pesticide Manual., Ed. Tomlin C. Royal Soc. of Chemistry/BCPC Crop Protection Publication, Batch Press, Bath. U.K. (1994)
Applebaum
   Biochemistry of Digestion. In: Comparative Insect Physiology, Biochemistry and Pharmacology (Ed. Kerkut G. A. and Gilbert L. I.). 1985 279–300. Permagon Press, London.
Barrett A. J.

Methods in Enzymology, 1944 244 1–15.

Blood D. C. and Studdert A.
　In: Bailliere's Comprehensive Veterinary Dictionary. Baillieve Tindall. Sydney. 1988 p899.

Bowles V. M., Feehan J. P. and Sandeman R. M.
　International Journal for Parasitology, 1990 20 169–174.

Broadway R. M.
　J. Chem. Ecol. 1989 15 2101–2113.

Broadway R. M. and Duffey S. A.
　Journal of Insect Physiology, 1986 34 1111–1117.

Burgess E. P. J. , Main C. A., Stevens P. S., Christeller J. T., Gatehouse A. M. R. and Laing W. A.
　Journal of Insect Physiology, 1994 40 803–814.

Christeller J. T., Laing W. T. Shaw B. D. and Burgess E. P. J.
　Insect Biochemistry, 1990 20 157–164.

Christeller J. T., Gatehouse A. M. R. and Laing W. A.
　Insect Biochemistry and Molecular Biology, 1994 24 103–109.

Christeller J. T., Laing W. A., Markwick N. P. Burgess E. P. J.
　Insect Biochemistry and Molecular Biology, 1992 22 735–746

Christeller J. T., Shaw B. D., Gardiner S. E. and Dymock J.
　Insect Biochemistry, 1989 19 221–231.

Cohen A. C.
　Journal of Insect Physiology, 1993 39 823–829.

Cornell J. A.
　In: Wiley Series in Probability and Mathematical Statistics. John Wiley and Sons Inc. USA.

Czapla T. H. (1993)
　Pioneer Hybrid International Patent (PCT) Application US94/00630 Publication No. WO94/16565.

Deloach J. R. and Spates G.
　Journal of Economic Entomology, 1980 73 590–594.

Dow J. A. T.
　Advances in Insect Physiology, 1986 19 187–328

Dymock J. J., Laing W. A., Shaw B. D., Gatehouse A. M. R., Christeller J. T.
　New Zealand Journal of Zoology, 1992 19: 123–131.

Eguchi M. and Iwamoto A
　Insect Biochemistry, 1976 6 491–496.

Eguchi M. and Kuriyama K.
　Journal of Biochemistry, 1986 97 1437–1445.

Ferreira C, Capella A. N., Sitnik R. and Terra W. R.
　Archives of Insect Biochemistry and Physiology, 1994 26 299–313.

Ferreira C. and Terra W. R.
　Arch. Biochem. Biophys., 1986 244 478–485.

Gatehouse A. M. R. and Boulter D.
　Journal of Food Science and Agriculture, 1983 34 345–350.

Hilder V. A., Gatehouse A. M. R., Sheerman S. E., Barker R. F. and Boulter D.
　Nature, 1987 330 160–163.

Hines M. E., Nielson S. S., Shade R. E. and Pomeroy M. A.
　Entomologia Exp. Appl., 190 57 201–207.

Houseman J. G., Philogene B. J. R. and Downe A. E. R.
　Canadian Journal of Zoology, 1989 67 864–868.

Ishaaya I., Moore I. and Joseph D.
　J. Insect Physiology, 1971 17 945–943

IUBMC (International Union of Biochemistry and Molecular Biology)
　In:Enzyme Nomenclature 1992 (Ed. Webb E. C.). Academic Press Inc., Orlando, Fla.

Jungreis A. M.
　In:Advances in Insect Physiology (Ed. Treherne J. E., Berridge M. J. and Wigglesworth V. B.) 1979 pp 193–183. Academic Press, London.

Larocque A. M. and Houseman J. G.
　Journal of Insect Physiology, 1990 36 691–697.

Lecadet M. M. and Dedonder R.
　Bull. Soc. Chim. Biol., 1966 48 631–660.

Lenz C. J., Kang J. S., Rice W. C., McIntosh A. H., Chippendale G. M. and Schubert K. R.
　Archives of Insect Biochemistry and Physiology, 1991 16 201–212.

Liang C., Brookhart G., Feng G. H., Reek G. R. and Kramer K. J.
　FEBS Letters, 1991 278 139–142.

MacIntosh S. C., Kishore G. M., Perlack F. J., Marrone P. G., Stone T. B., Sims S. R. and Fuchs R. L.
　Journal of Agriculture and Food Chemistry, 1990 3 1145–1151.

McDonald J. K.
　Histochemical Journal, 1985 17 773–785.

McGhie T. K., Christeller J. T., Ford R. and Allsop P. G.
　Archives of Insect Biochemistry and Physiology, 1995 28 351–363.

Miller J. W., Kramer K. J. and Law J. H.
　Comparative Biochemistry and Physiology, 1974 48B 117–129.

Mohamed B. B. H. and Attias J.
　Insect Biochemistry, 1987 17: 653–658.

Mullens B. A. and Rodriquez J. L.
　Journal of Econ.Entomology, 1992 85 137–143.

Orr G. L., Strickland J. A. and Walsh T. A
　Journal of Insect Physiology, 40: 893–900.

Prakash I.
　Entomon., 1992 17 15–19.

Pritchett D. W., Young S. Y. and Geren C. R.
　Insect Biochemistry, 1981 11 523–526.

Prowning R. F. and Irzykiewicz H.
　Journal of Insect Physiology, 1962 8 275–284.

Sakal E., Applebauum S. W. and Birk Y.
　International Journal of Protein Research, 1989 34 498–505.

Samuels R. I., Charnley A. K. and Reynolds S. E.
　Insect Biochemistry and Molecular Biology, 1993 23 615–620.

Samuels R. I. and Paterson I. C.
　Comparative Biochemistry and Physiology, 1995 110B 661–669.

Sandeman R. M., Feehan J. P., Chandler R. A. and Bowles V. M.
　International Journal for Parasitology, 1990 20 1019–1023

Santos C. D. and Terra W. R.
　Insect Biochemistry, 1984 14 587–594.

Sasaki T. and Suzuki Y.
　Biochimica et Biophysica Acta, 1982 703 1–10.

Shade, R. E., Murdoch, L. L., Foard, D. E., Pomeroy, M. A.
　Environmental Entomology, 1986 15 1286–1291

Sheuvi A. B. (1983)
　E. I. DuPont de Nemours and Co. Wilmington Del. U.S. Pat. No. 4,537,773.

Shuckle R. H. and Murdoch L. L.
  Environmental Entomology, 1983 12 787–791.
Taylor A.
  Trends in Biological Sciences, 1993a 18 167–171.
Taylor A.
  The FASEB Journal 1993b 7 290–298.
Teo L. H., Hammond A. M., Woodring J. P. and Fescemeyer H. W.
  Annals of the Entomological Society of America, 1990 83 820–826.
Terra, W. R. and Ferreira, C.
  Comp. Biochem. Physiol., 1994 109B 1–62
Thie N. M. R. and Houseman J. G.
  Insect Biochemistry, 1990 20 313–318.
Tomalia D. A. and Wilson L. R. (1985).
  The Dow Chemical Company U.S. Pat. No. 4,517,122.
Tomalia D. A. and Wilson L. R. (1986)
  The Dow Chemical Company U.S. Pat. No. 4,600,535.
Ward C. W.
  Australian Journal of Biological Science, 1975a 28 1–23.
Ward C. W.
  Biochimica et Biophysica Acta, 1975b 384 215–227.
Wolfson J. L. and Murdock L. L.
  Entomologia Exp. Appl., 1987 44 235–240.
Tomalia D. A. and Wilson L. R. (1985).
  The Dow Company U.S. Pat. No. 4,517,122.
Tomalia D. A. and Wilson L. R. (1986).
  The Dow Company U.S. Pat. No. 4,600,535.
Ward C. W.
  Australian Journal of Biological Science, 1975a 28 1–23.
Ward C. W.
  Biochimica et Biophysica Acta, 1975b 384 215–227.
Wolfson J. L. and Murdock L. L.
  Entomologia Exp. Appl., 1987 44 235.

We claim:

1. The method of controlling insects comprising the step of exposing said insects to a composition comprising an aminopeptidase inhibitor or metallopeptidase inhibitor, and further comprising a non-strongly-chelating peptidase inhibitor, together with a veterinarily agriculturally or horticulturally acceptable carrier.

2. The method according to claim 1, wherein the said aminopeptidase inhibitor or metallopeptidase inhibitor comprises an amino group or derivative thereof.

3. The method according to claim 1, wherein the said aminopeptidase inhibitor or metallopeptidase inhibitor comprises one or more amino acid moieties or derivatives thereof.

4. The method according to claim 1, wherein the said aminopeptidase inhibitor or metallopeptidase inhibitor comprises a leucine, valine, methionine, glutamine, cysteine, aspartate, proline arginine or alanine moiety, or a derivative thereof.

5. The method according to claim 1, wherein the said aminopeptidase inhibitor or metallopeptidase inhibitor comprises a leucine moiety or a derivative thereof.

6. The method according to claim 1, wherein the said aminopeptidase inhibitor or metallopeptidase inhibitor interacts with metal ions in the active site of the metallopeptidase or aminopeptidase.

7. The method of claim 1, wherein the said aminopeptidase inhibitor or metallopeptidase inhibitor comprises a chelating agent or has chelating activity.

8. The method according to claim 7, wherein the said aminopeptidase inhibitor or metallopeptidase inhibitor comprises a bidentate, tridentate, quadridentate or hexadentate chelating agent.

9. The method of claim 7, wherein the said chelating agent comprises an amino carboxylic acid moiety or nitrilo triacetic acid, or a salt or derivative thereof having chelating activity.

10. The method of claim 7, wherein the said chelating agent comprises ethylene diamine tetraacetic acid, or a salt or derivative thereof having chelating action.

11. The method of claim 1, wherein the said aminopeptidase inhibitor or metallopeptidase inhibitor comprises a transition metal ion or a complex or derivative of said ion, wherein the ion is selected from the group consisting of copper, cobalt, zinc, magnesium, manganese, vanadium and iron.

12. The method of claim 1, wherein the said aminopeptidase inhibitor or metallopeptidase inhibitor comprises a boronic, phosphoryl or phosphonyl moiety.

13. The method of claim 1, wherein the said aminopeptidase inhibitor or metallopeptidase inhibitor binds irreversibly to an aminopeptidase or metallopeptidase.

14. The method of claim 1, wherein the said aminopeptidase inhibitor or metallopeptidase inhibitor does not inhibit trypsin or calpain.

15. The method of claim 1, wherein the said aminopeptidase inhibitor or metallopeptidase inhibitor does not inhibit serine or cysteine peptidases.

16. The method of claim 1, wherein the said inhibitor inhibits the activity of an enzyme selected from the group consisting of leucine aminopeptidases, aminopeptidases of type A, B, N and M, arginine aminopeptidases, methionine aminopeptidases, D-amino acid aminopeptidases, peptidyl dipeptidases, zinc aminopeptidases, N-formyl methionine aminopeptidases, dipeptidyl-aminopeptidases, carboxypeptidases of type A and B, tripeptidyl peptidases, dipeptidyl peptidases and peptidyl-tripeptidases.

17. The method of claim 1, wherein the said inhibitor inhibits the activity of a leucine aminopeptidase.

18. The method of claim 17, wherein the said inhibitor inhibits the activity of an insect leucine aminopeptidase.

19. The method of claim 1, wherein the said non-strongly-chelating peptidase inhibitor, comprises a serine peptidase inhibitor, a cysteine peptidase inhibitor, an aspartyl peptidase inhibitor, a metallopeptidase inhibitor, or an aminopeptidase inhibitor.

20. The method according to claim 19, wherein the said non-strongly-chelating peptidase inhibitor is selected from the group consisting to trypsin and chymotrypsin inhibitors.

21. The method according to claim 19, wherein the said non-strongly-chelating peptidase inhibitor is selected from the group consisting of serine or cysteine peptidases inhibitors derived from legumes, vegetables, fruits or cereals.

22. The method according to claim 19, wherein the said non-strongly-chelating peptidase inhibitor is selected from the group consisting of cystatins and E-64.

23. The method according to claim 19, wherein the said non-strongly-chelating peptidase inhibitor comprises a potato carboxypeptidase inhibitor.

24. The method according to claim 19, wherein the said non-strongly-chelating peptidase inhibitor comprises Eglin C.

25. The method according to claim 19, wherein the said non-strongly-chelating peptidase inhibitor comprises 4-(2-aminoethyl)-benzenesulfonylfluoride hydrochloride (PEFABLOC).

26. The method according to claim 1, wherein the said composition comprises soya bean trypsin inhibitor (SBTI) and EDTA.

27. The method according to claim 1, wherein the said composition comprises L-leucinethiol and EDTA.

28. The method according to claim 1, wherein the said composition comprises 4-(2-aminoethyl)-benzenesulfonylfluoride hydrochloride (PEFABLOC).

29. The method of claim 1, wherein the said composition comprises actinonin and soya bean trypsin inhibitor (SBTI).

30. The method of claim 1, wherein the said composition comprises L-leucinethiol and soya bean trypsin inhibitor (SBTI).

31. The method of claim 1, wherein the said composition comprises 1,10-phenanthroline and SBTI.

32. The method of claim 1, wherein the said composition comprises Bestatin and soya bean trypsin inhibitor (SBTI).

33. The method of claim 1, wherein the said composition comprises antipain and EDTA.

34. The method of claim 1, wherein the said aminopeptidase inhibitor or non-strongly-chelating peptidase inhibitor comprises a peptide, polypeptide or protein moiety.

35. The method of claim 1, comprising the step of exposing insect eggs or insect larvae to the said composition, whereby the hatching of insect eggs and/or the development of insect larvae is inhibited.

36. The method according to claim 1, wherein the insect is of an order selected from the group consisting of Lepidoptera, Hemiptera, Dictyoptera, Orthoptera, Coleoptera, Psocoptera, Isoptera, Thysanoptera, Hymenoptera, Homoptera, Diptera, Anoplura, Malophaga and Siphonaptera.

37. The method according to claim 1, wherein the insect is selected from the group consisting of myiasis lies, fleas, cockroaches, light brown apple moths, crickets, budworms, and insects that infest stored grain or grain products.

38. The method according to claim 1, wherein the composition is administered by topical, oral or parenteral means.

39. The method according to claim 1 wherein the composition is administered by topical means.

40. The method according to claim 1, wherein the compositions are administered to a plant selected from the group consisting of cotton, oil seed crops, ornamental plants, flowers, fruit trees, cereal crops, vine crops, root crops, pasture plants and vegetables.

* * * * *